(12) United States Patent
Booker et al.

(10) Patent No.: US 7,624,868 B2
(45) Date of Patent: Dec. 1, 2009

(54) PIPETTE HOLDER

(75) Inventors: Robert Booker, Vandergrift, PA (US); Dustin John Arabia, New Kensington, PA (US); Benjamin T. Ewing, Cranberry, PA (US); Christopher Nick Magalich, Avonmore, PA (US)

(73) Assignee: Cook Vascular Incorporated, Leechburg, PA (US)

( * ) Notice: Subject to any disclaimer, the term of this patent is extended or adjusted under 35 U.S.C. 154(b) by 257 days.

(21) Appl. No.: 11/602,593

(22) Filed: Nov. 21, 2006

(65) Prior Publication Data

US 2007/0125675 A1 Jun. 7, 2007

Related U.S. Application Data

(60) Provisional application No. 60/741,135, filed on Dec. 1, 2005.

(51) Int. Cl.
*A61B 17/06* (2006.01)
*A61B 19/02* (2006.01)
*A61L 15/00* (2006.01)

(52) U.S. Cl. .................. 206/438; 206/305; 206/363; 206/443; 206/370

(58) Field of Classification Search .............. 206/438, 206/305, 380, 363, 365, 443, 366, 370; 221/303
See application file for complete search history.

(56) References Cited

U.S. PATENT DOCUMENTS

| 2,624,011 | A | * | 12/1952 | Stern .................. 250/475.2 |
| 3,272,319 | A | * | 9/1966 | Brewer .................. 206/569 |
| 4,271,979 | A | * | 6/1981 | Manz .................... 221/288 |
| 4,514,091 | A | * | 4/1985 | Kaspar et al. ............ 366/130 |
| 4,520,926 | A | * | 6/1985 | Nelson .................. 206/366 |
| 4,600,112 | A | * | 7/1986 | Shillington et al. ....... 215/274 |
| 4,801,013 | A | * | 1/1989 | Bruno ................... 206/366 |
| 4,859,423 | A | * | 8/1989 | Perlman ................. 422/102 |
| 5,495,941 | A | * | 3/1996 | Leonard ................. 206/366 |
| 5,803,638 | A | * | 9/1998 | Gueret .................. 401/122 |
| D404,646 | S | * | 1/1999 | Black et al. .............. D9/446 |
| 6,375,028 | B1 | * | 4/2002 | Smith .................... 220/258.1 |
| 2004/0159579 | A1 | * | 8/2004 | Winckels et al. .......... 206/581 |
| 2007/0034630 | A1 | * | 2/2007 | Lancesseur et al. ....... 220/281 |

* cited by examiner

*Primary Examiner*—Ehud Gartenberg
*Assistant Examiner*—Blaine G Neway
(74) *Attorney, Agent, or Firm*—Brinks Hofer Gilson & Lione

(57) ABSTRACT

A holder for a micro-sized medical device, such as a pipette, includes a main body portion having an interior space sized for housing at least one pipette. A reducing insert comprising a sleeve has an open end and a substantially closed end. The sleeve is sized such that the open end is receivable in the main body portion through an open axial end of the main body, and the substantially closed end has an aperture extending therethrough having a diameter sufficient for passage of a pipette therethrough. An end cap is engageable with the open axial end of the main body portion, and is selectively movable between an open position wherein the interior space of the main body communicates via the aperture with an environment exterior of the holder, and a closed position wherein the seal covers the aperture. The components of the holder may be formed integrally or separately.

6 Claims, 11 Drawing Sheets

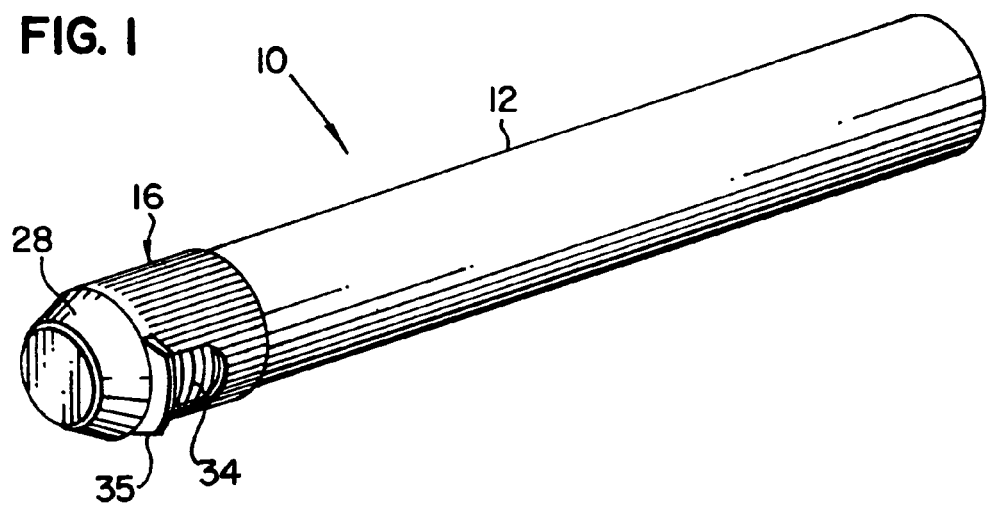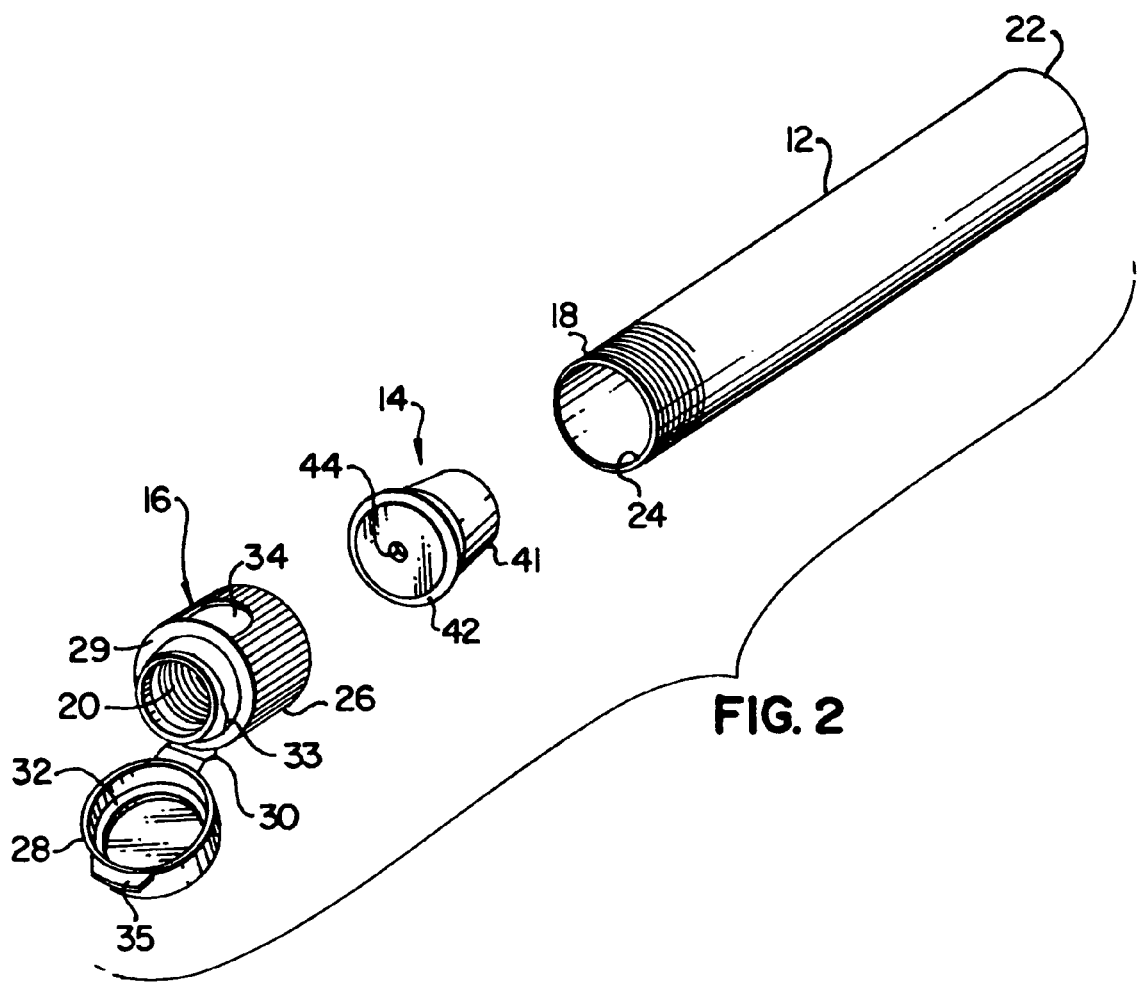

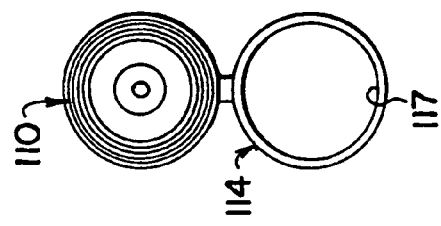
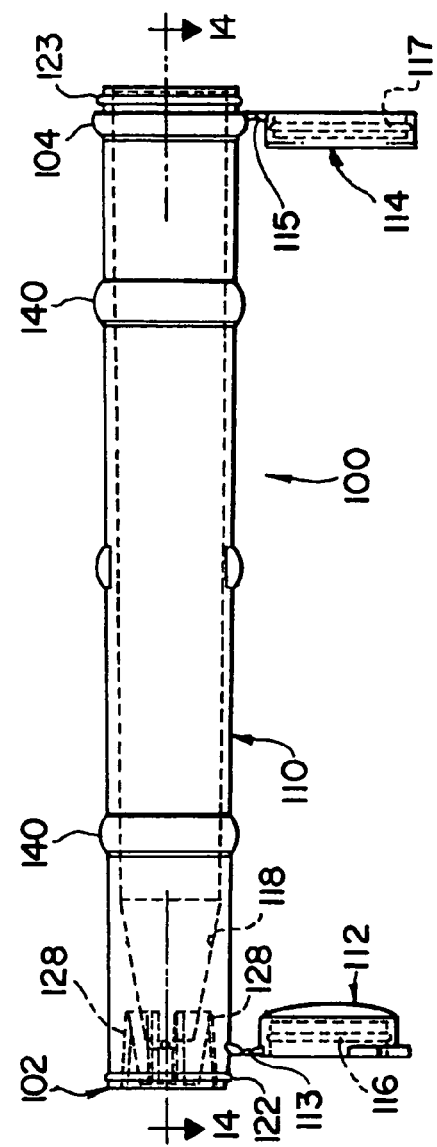
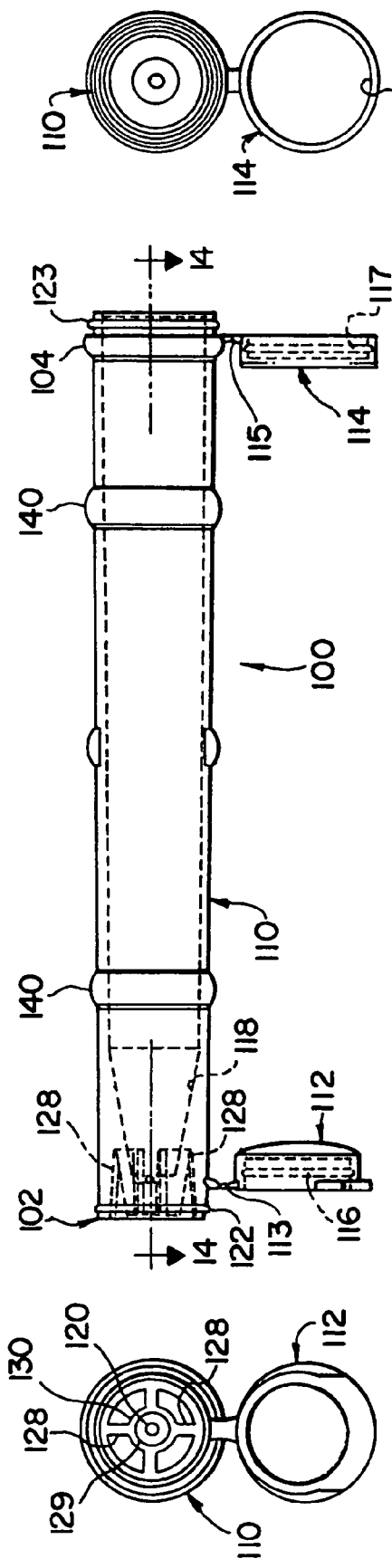
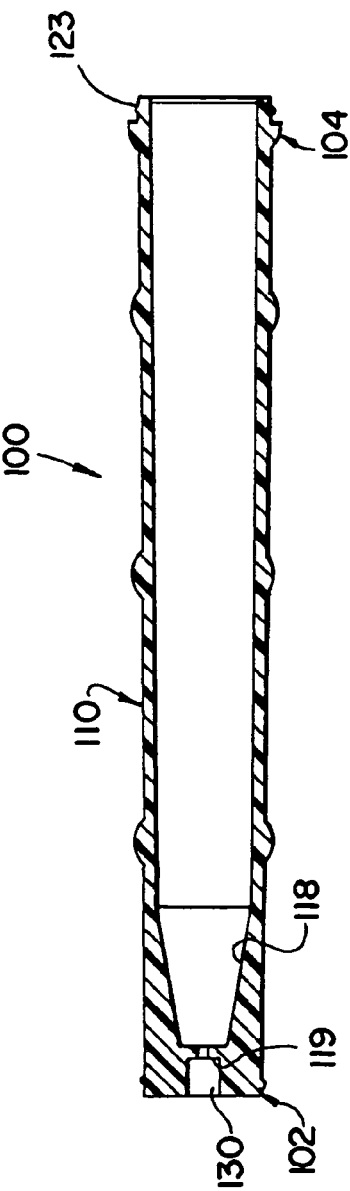

PIPETTE HOLDER

RELATED APPLICATION

The present patent document claims the benefit of the filing date under 35 U.S.C. §119(e) of Provisional U.S. Patent Application Ser. No. 60/741,135, filed Dec. 1, 2005, which is hereby incorporated by reference.

BACKGROUND

1. Technical Field

The present application relates to a holder for medical devices, and more particularly, to a holder for pipettes suitable for use in micro-manipulation techniques, such as intracytoplasmic sperm injection.

2. Background Information

With the continuous advances of modern medicine, there is an ongoing need for increasingly smaller medical devices that are suitable for carrying out medical techniques on a micro scale not previously possible. With the advent of increasingly smaller devices, there is a corresponding increase in the number of micro portions of the devices, micro size accessories, and/or micro scale containers suitable for safely housing the devices and/or accessories. Notwithstanding the small scale of these micro size devices, accessories, etc., the need to maintain the structural strength and integrity, and the cleanliness and sterility of the devices has not diminished. In fact, due to the small size of such devices and the increasing sophistication of medical diagnostic and treatment instrumentation, in many cases the need for protection against breakage and/or contamination of micro devices is greater than with larger devices.

As a part of this trend toward micro-medicine, the use of small diameter pipettes that are suitable for aspirating and/or delivering very small volumes has dramatically increased. One example of a field of medicine that has experienced an increased use of such micro-size pipettes is the field of fertility treatment. Pipettes used in this field, commonly referred to as denuding pipettes, are typically used in micro treatment techniques such as in vitro fertilization (IVF) and intracytoplasmic sperm injection (ICSI). These fields, and others, continue to grow as more sophisticated micro-manipulation techniques are developed.

For example, in order to carry out ICSI, a single sperm is directly injected, under microscopic vision, into the cytoplasm of an oocyte. In order to prepare for this injection, the single sperm must be isolated, and aspirated into a microinjection pipette. Another pipette is used to hold the oocyte in position as the sperm is injected into the cytoplasm. Prior to injection, a denuding pipette then is used to denude the cumulus mass from the oocyte. It would not be possible to perform such delicate manipulation techniques without the use of reliable micro-scale devices.

Generally, denuding pipettes of the type described above are housed in containers that are designed to hold a multiplicity of such pipettes. The holder often has a common size, even when pipettes of different lengths are to be housed therein. Alternatively, numerous pipettes of a particular length may be housed in a container more suitable for pipettes of a different length. Given the fragile nature of such pipettes, and particularly the fragile nature of the tapered pipette tips, it would be preferred to house them in a container having a housing compartment specifically sized for pipettes of a specified length. In this way, unnecessary movement of the pipettes within the container can be minimized.

In addition to the foregoing, existing housings for micro-size pipettes are often structured in a manner such that the pipettes may contact and rest against the side walls of the container. After a period of time, and pursuant to movement of the pipettes within the holder, static electricity builds up in the housing and along the outer surface of the pipettes due to contact between the pipettes and the wall of the housing. Such static electricity can be disconcerting to the physician or other medical professional upon removal of a charged pipette from the container, and can result in multiple pipettes clinging to each other. It would be preferred to provide a housing containing features that minimize or eliminate the presence or formation of static electricity within the housing.

Existing micro-size pipette holders also often contain a screw-cap or like structure that is removed when a pipette is to be removed from the container. When the container holds a plurality of pipettes, the medical professional may inadvertently touch and/or withdraw more than one pipette during the removal of a single pipette. This undesired touching and/or removal of a pipette can introduce contamination into the container. Due to the very small size of such pipettes, even a small amount of contamination can be problematic when the pipette is later used in a medical procedure. In order to minimize the possibility of contamination, it would be preferred to minimize, or eliminate entirely, the possibility of removal of more than one pipette from a container at a time.

It is desired to provide a holder for a medical device, such as a micro-size pipette, that avoids the problems encountered with prior art holders. In particular, it is desired to provide a holder for pipettes that reduces the possibility of breakage of the pipettes, that reduces or eliminates the build-up of static electricity in the holder, and that is structured such that only a single pipette is exposed to the exterior environment upon removal of a pipette from the holder. It is particularly desired to provide such a holder for use with denuding pipettes.

BRIEF SUMMARY

The present invention addresses the problems existing in the prior art. In one form thereof, the present invention comprises a holder for a medical device. The holder includes an elongated main body portion, a reducing insert, and an end cap. The main body portion has a closed axial end and an open axial end, and an interior space sized for housing at least one medical device therein. The reducing insert includes a sleeve having an open end and a substantially closed end. Preferably, the sleeve is sized such that the sleeve open end is receivable in the main body portion through the open axial end, and the substantially closed end has an aperture extending therethrough and communicating with the interior space. The aperture has a diameter sufficient for passage of the medical device therethrough. The end cap includes a base portion and a seal portion. The base portion is engageable with the open axial end of the main body portion. The seal portion is engaged with the base portion and movable relative thereto between an open position wherein the interior space of the main body portion communicates via the aperture with an environment exterior of the holder, and a closed position wherein the seal covers said aperture.

In another form thereof, the invention comprises a holder for an elongated medical device, such as a pipette. The holder comprises a main body portion having a first axial end and a second axial end, and an interior space disposed between the axial ends. The interior space is sized for housing at least one pipette therein. The second axial end has an aperture extending therethrough, wherein the aperture has a diameter dimensioned for permitting passage of a single pipette therethrough at any one time. An end cap is provided at the second axial end for selectively closing the end.

BRIEF DESCRIPTION OF THE DRAWINGS

FIG. 1 is a perspective view of a pipette holder according to an embodiment of the present invention;

FIG. 2 is an exploded view of the pipette holder shown in FIG. 1, showing a cap in the open position;

FIG. 13 is a side view of the pipette holder of FIG. 12;

FIG. 14 is a sectional view of the pipette holder of FIG. 13, taken along lines 14-14 of FIG. 13;

FIG. 15 is an end view of the pipette holder of FIG. 12; and

FIG. 16 is an end view from the opposite end of the pipette holder of FIG. 12.

DETAILED DESCRIPTION OF THE DRAWINGS AND THE PRESENTLY PREFERRED EMBODIMENTS

Figure 3:
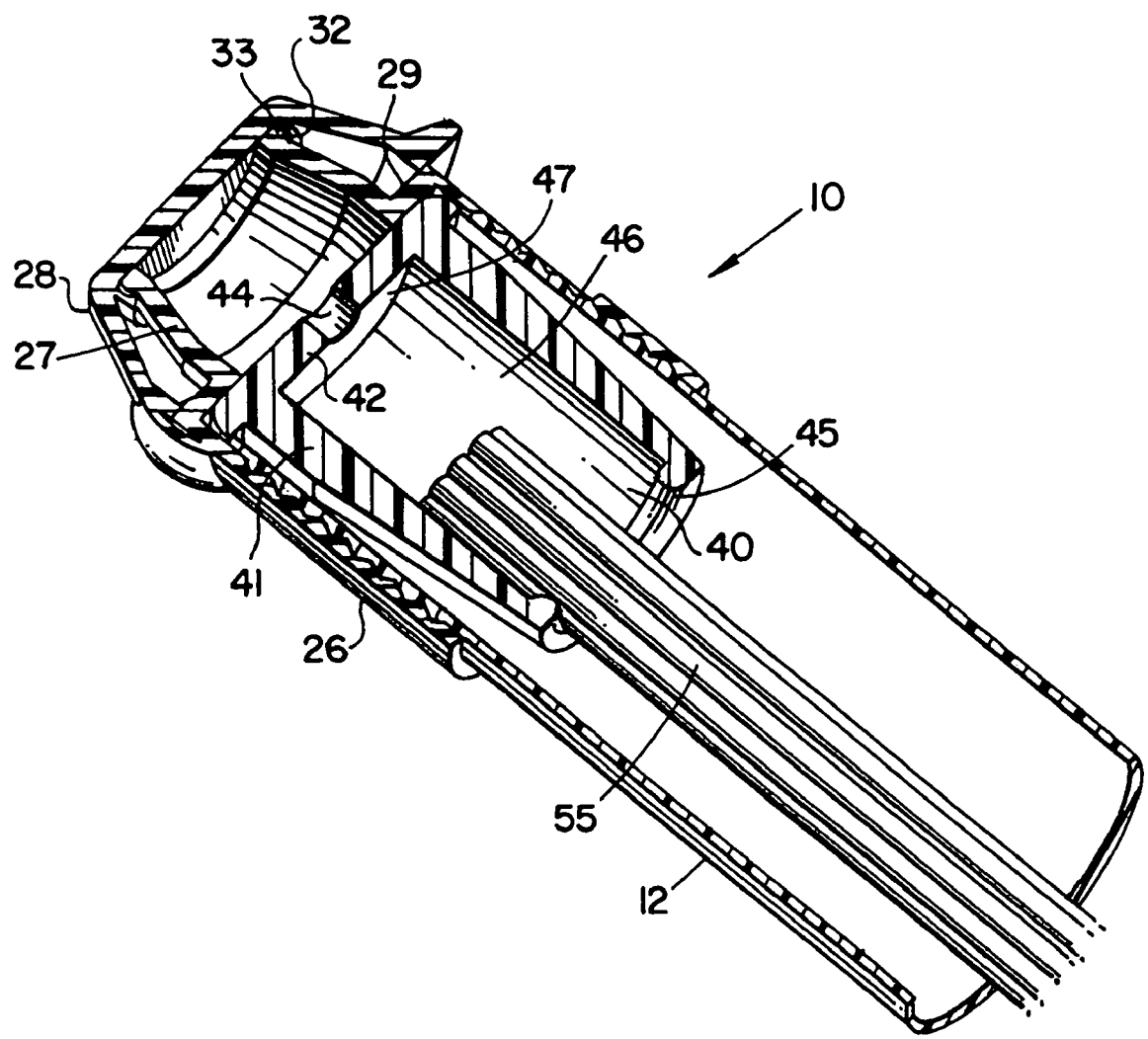
FIG. 3 is a longitudinal sectional view of a portion of the pipette holder of FIG. 1.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention comprises a holder for a medical device. In a preferred embodiment, the invention comprises a holder for a micro-size medical device, such as a pipette. One preferred example of such a micro-size pipette is a pipette, such as a denuding pipette. In the following discussion, the medical device housed in the inventive holder will generally be described simply as a pipette. However, those skilled in the art will appreciate that the inventive holder can also be used for housing other medical devices, as well as pipettes of other shapes and sizes, and that the scope of the invention is intended to encompass all such devices.

FIG. 1 is a perspective view of a holder 10 for one or more medical devices, such as pipettes, according to an embodiment of the present invention. FIG. 2 is an exploded view of the holder of FIG. 1, illustrating the components that comprise the holder. As shown in FIG. 2, holder 10 comprises a main holder body 12, a reducing insert 14, and a cap 16. When the device is fully assembled as shown in FIG. 1, cap 16 is engaged with main body 12 at an end portion of the main body. In the embodiment shown, cap 16 is provided with internal screw threads 20 that are capable of threaded engagement with external screw threads 18 of main body 12 in conventional fashion. Those skilled in the art will appreciate that other conventional attachment mechanisms, such as a friction fit, a snap fit, and the like, can be substituted for the threaded engagement shown in the figures.

In order to avoid undue axial movement of the medical devices within the holder, the main housing body 12 has a length closely approximating the length of the devices, such as pipettes, to be housed therein. Although a certain amount of axial movement may be permissible, it is preferred to avoid such movement to the extent possible, to minimize the possibility of damage to the pipettes due to uncontrolled and/or excessive movement within the holder. In many cases, a pipette will have a length of about three inches. In this event, the length of main body 12 is preferably about 0.25 inch longer than the length of the pipette. For best results, the main body should not have a length greater than about one inch, preferably 0.50 inch, and more preferably 0.25 inch, of the length of the pipette.

In this embodiment, the main body 12 comprises a hollow cylindrical-type structure, having a sealed end 22 and an open end 24. Although end 22 is shown in the figures as a permanently sealed end, those skilled in the art will appreciate that the seal need not always be a permanent seal. Rather, a screw cap or like structure can be provided at end 22 to provide access to the interior space of main body 12 for inserting or removing the medical device(s), such as pipette(s) housed within holder 10.

Preferably, the main body 12 has a rigid or semi-rigid construction, such that undue flexing or bending of the main body is minimized or even eliminated altogether. One particularly preferred composition from which to form main body 12 is an extrudable resin, such as cellulose acetate propionate (CAP). Although extrudable resins such as CAP are preferred, virtually any conventional container composition can be utilized, such as plastic, glass, or metal.

A feature of this embodiment is the presence of the reducing insert 14. Reducing insert 14 comprises a generally cylindrical hollow structure. This structure comprises a sleeve portion 41 that is open at one end 40 and substantially closed at the other end by a larger diameter end portion 42. This arrangement may be best visualized in FIGS. 3 and 5. An optional spacer, such as ring 45, may be provided at open end 40 or otherwise along the length of sleeve portion 41 for spacing pipettes 55 from the inner wall surface 46 of sleeve portion 41. Although FIG. 3 illustrates the presence of a single spacing ring, one or more additional structures can be spaced in the direction of end portion 42 along the inner surface of sleeve portion 41.

End portion 42 includes an aperture 44 that extends therethrough and communicates with the interior space of main body 12 when the holder is fully assembled. Aperture 44 is preferably sized such that only a single pipette can be passed through the aperture at any one time. The diameter of aperture 44 will thus generally vary depending upon the diameter of the pipettes or other medical devices being housed in the inventive holder 10. When the medical device comprises a denuding pipette, the diameter of the aperture will normally vary between about 0.035 and 0.081 inch, dependent upon the size of the denuding pipette.

As shown in FIG. 3, sleeve portion 41 of the reducing insert is sized such that it fits into open end 24 of holder main body 12. In the preferred embodiment shown, end portion 42 of the reducing insert has a larger diameter than the diameter of open end portion 24 of main holder body 12. As a result, main body open end portion 24 essentially acts as a stop to prevent further axial movement of reducing insert end portion 42, and hence, to prevent further movement of reducing insert 14 itself within the interior environment of holder main body 12. Reducing insert 14 may favorably be formed from polymers, such as polyethylene and polypropylene. However, numerous other plastic, glass and metal compositions may be substituted.

It is preferred to form reducing insert 14 such that the underside of end portion 42 is substantially flat. Prior art containers generally have an inner lid that tapers toward the center of the lid, thereby causing multiple pipettes to funnel toward the center. By providing a flat inner surface, the pipettes are not funneled or otherwise urged toward the center. In this way, when a single pipette is to be withdrawn, multiple other pipettes are not being funneled into the same space, thereby facilitating the withdrawal of a single pipette.

Cap 16 comprises a generally cylindrical base portion 26 and a seal portion 28. Preferably, seal portion 28 is pivotally connected to base portion 26 by a hinged connection, such as living hinge 30. Base portion 26 has an inner diameter along at least part of its inner surface that is slightly larger than the outer diameter of threaded portion 18 of main body 12. In this manner, inner screw threads 20 of cap 16 can be threadably received on external screws 18 of main housing body 12.

Figure 4:
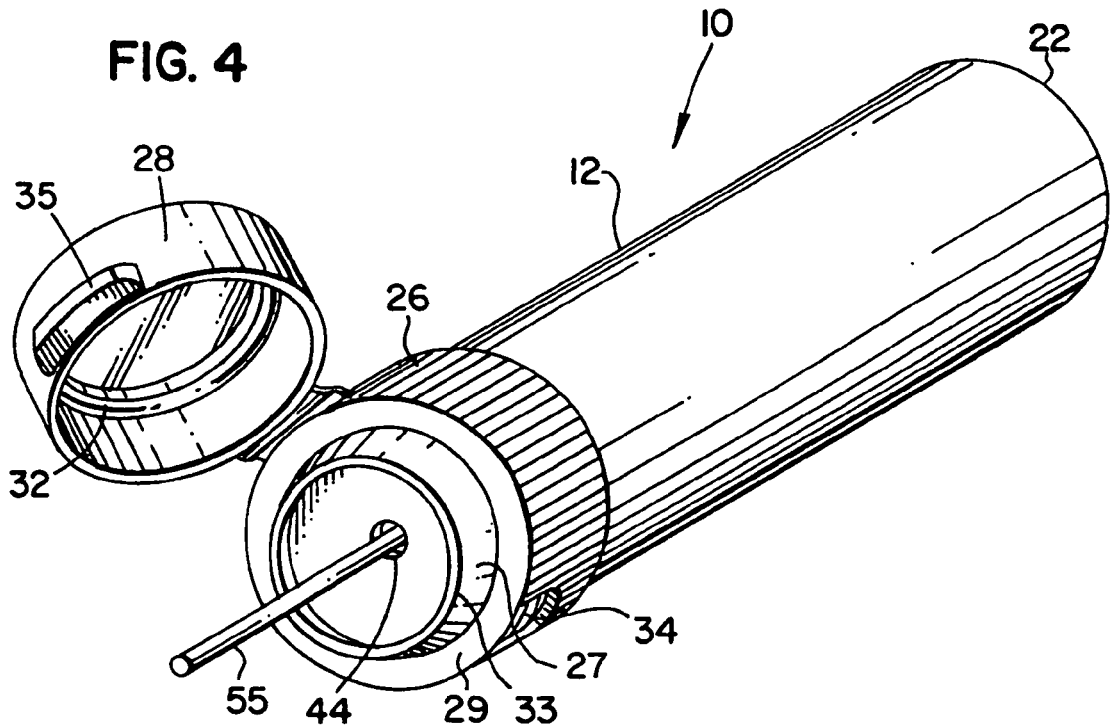
FIG. 4 is a perspective view of the pipette holder of FIG. 1 with the cap in the open position, and showing a pipette partially dispensed therefrom.
Figure 5:
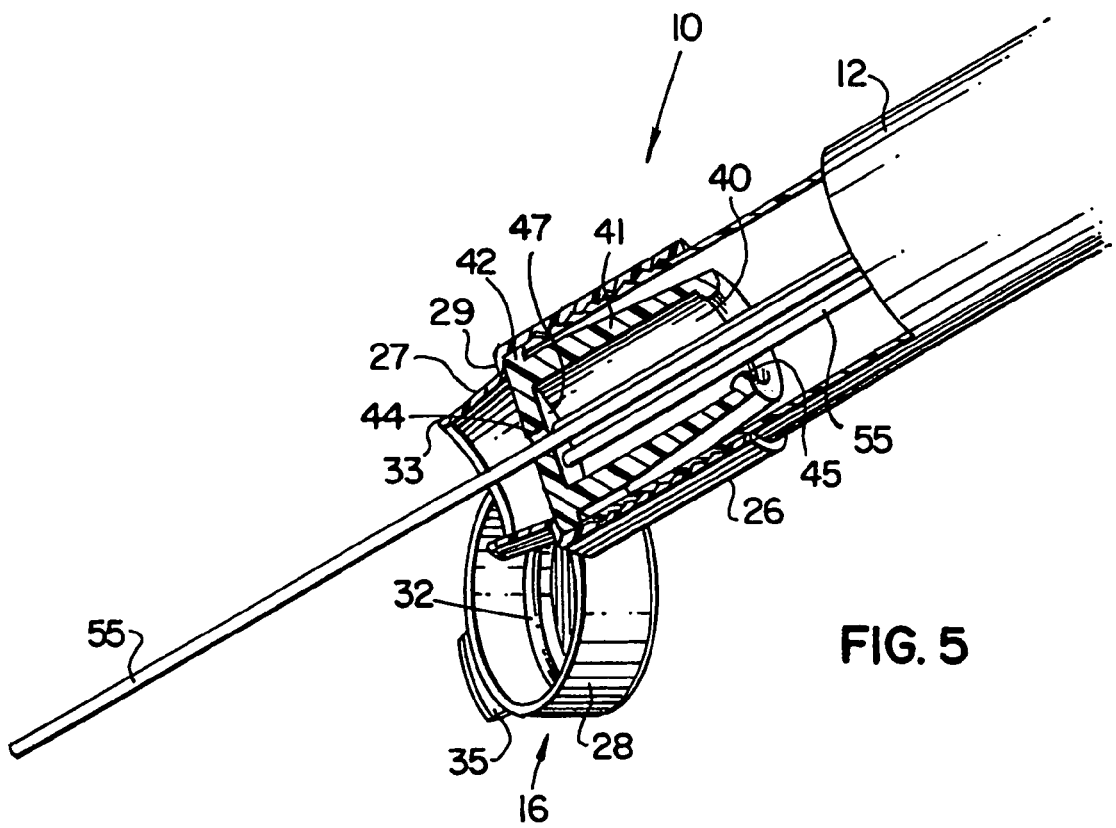
FIG. 5 is a view, partially in section, of a portion of the pipette holder as shown in FIG. 4 with the cap in the open position, and showing a pipette partially dispensed therefrom.

Cylindrical base portion 26 includes a smaller diameter extension 27, and a shoulder 29 that interconnects the base portion 26 and the small diameter extension 27. Base portion 26 and seal portion 28 cap are provided with appropriate structure to enable a snap fit connection therebetween. In this manner, the cap is selectively movable between a closed position, as shown in FIGS. 1 and 3, and an open position, as shown in FIGS. 2, 4 and 5. Preferably, a snap ring 32 is provided on the interior circumferential surface of seal portion 28, and a corresponding ring or analogous structure 33 is provided on small diameter extension portion 27 of base portion 26. Cap 16 may then simply be closed by pivoting seal portion 28 along hinge 30, and snapping it onto corresponding ring 33 of small diameter extension 27.

In the embodiment shown, an optional finger or thumb portion 34 may be provided along the outer surface of cap base portion 26, and a corresponding tab 35 may be provided on the cap seal portion 28. Finger/thumb portion 34 and tab 35 cooperate to allow a user to selectively open or close cap seal portion 28 in well-known fashion, by simply "flicking" the seal portion away from the remainder of cap 16. The features of the cap described herein are generally similar to those presently provided on many conventional structures, such as toothpaste caps. Those skilled in the art will appreciate that other conventional closure mechanisms may be substituted, and are considered within the scope of the invention.

When cap 16 is to include a living hinge 30 as illustrated, it is preferred to utilize a polymeric composition, such as polypropylene, from which a living hinge may be readily molded or otherwise fabricated. However, those skilled in the art may readily select other materials from which a living hinge may be favorably formed. If the cap is not to include a living hinge, then numerous other compositions can be substituted. Those skilled in the art are readily able to select a suitable composition in view of the intended use of the cap.

As yet another feature of the invention, cap 16 and/or holder 10 may be color-coded based upon the size of the cap and of the holder. In this manner, a specific color may be used to indicate the size of the denuding pipette or other device housed in the particular holder.

The inventive pipette holder 10 is preferably sized to accommodate between about 1 to 10 pipettes; however the holder may also be sized to accommodate larger numbers of pipettes if desired. FIG. 3 illustrates an arrangement wherein a plurality of denuding pipettes 55 is housed within holder 10. One well-known example of a typical denuding pipette is sold by Cook Incorporated of Bloomington, Ind., under the name FLEXIPET®. Micro-size pipettes, including but not limited to denuding pipettes, are known in the art, and need not be further described herein to gain an understanding of the present invention. For best results, the length of holder 10 will be linked to the length of the pipettes. In the embodiment shown, the pipettes extend from the bottom of holder 10 (not shown) substantially to the top of the holder. The pipettes should extend upwardly from bottom end 40 of the reducing insert 14 a selected distance into the interior space of the reducing insert as shown. Preferably, the pipettes will extend roughly one-half the length of sleeve portion 41 of the reducing insert. As a result, the reducing insert essentially holds the pipettes within the interior of the holder. This arrangement prevents substantial movement of the pipettes within the holder, and inhibits substantial contact between the pipettes and the inner side walls of holder main body 12.

When not properly controlled, excessive movement of the pipettes within the holder may cause breakage or other damage to the pipette. The presence of an internal structure, such as the reducing insert shown and described, hinders excessive movement, thereby diminishing the possibility of such breakage or damage. When the pipettes are not prevented from substantial contact with the inner side walls of the holder, static electricity may build up in the pipettes, apparently due to excessive rotation or other movement of the pipettes when in contact with the side walls. It can be disconcerting to physicians and other medical professionals when an electrically charged pipette is removed from the holder. In addition, a buildup of static electricity in the holder may cause the pipettes in the holder to cling to each other, thus hindering easy removal of a single pipette from the holder.

Figure 6:
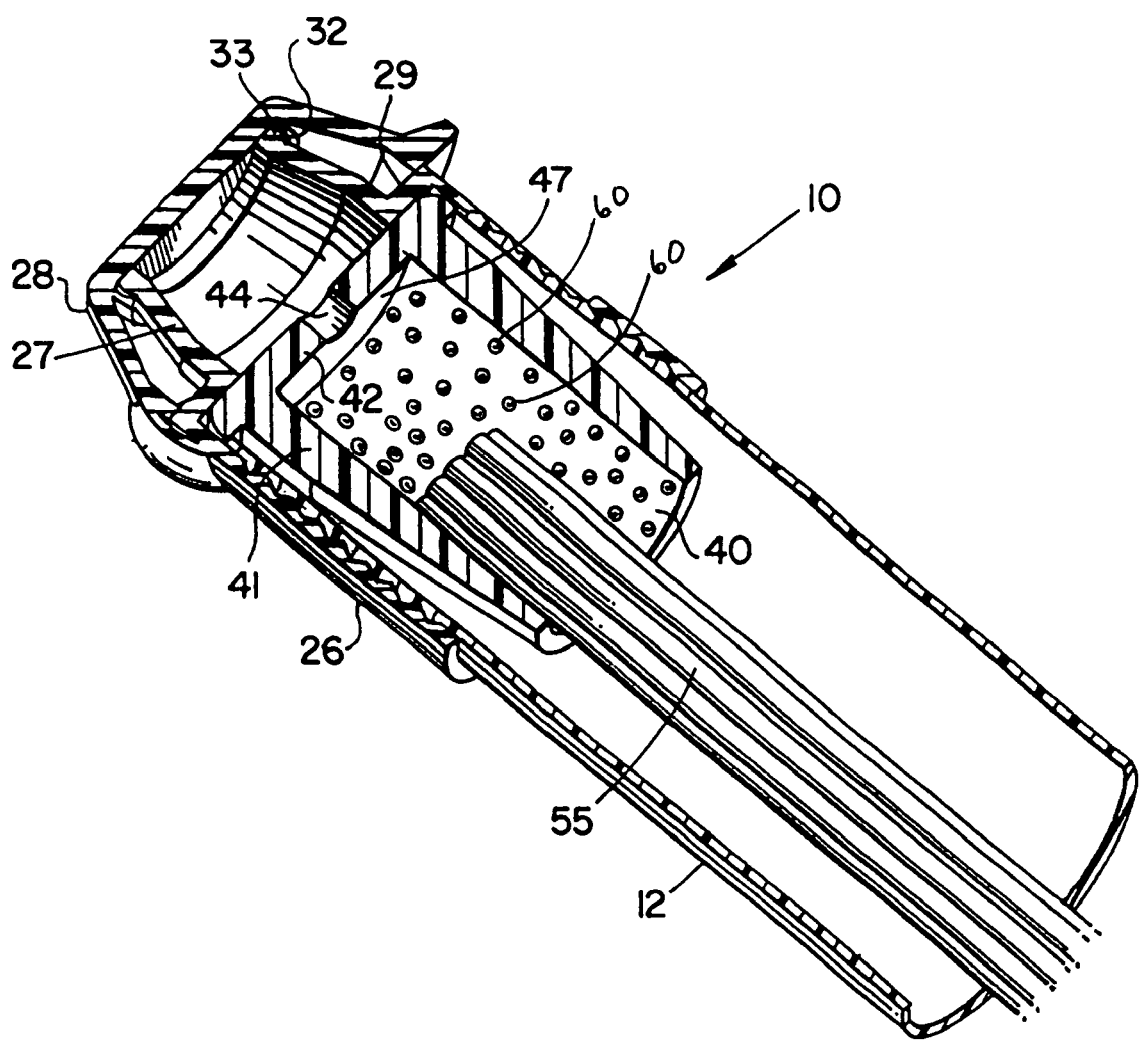
FIGS. 6-11 comprise alternative designs of the inner surface of the reducing insert.
Figure 7:
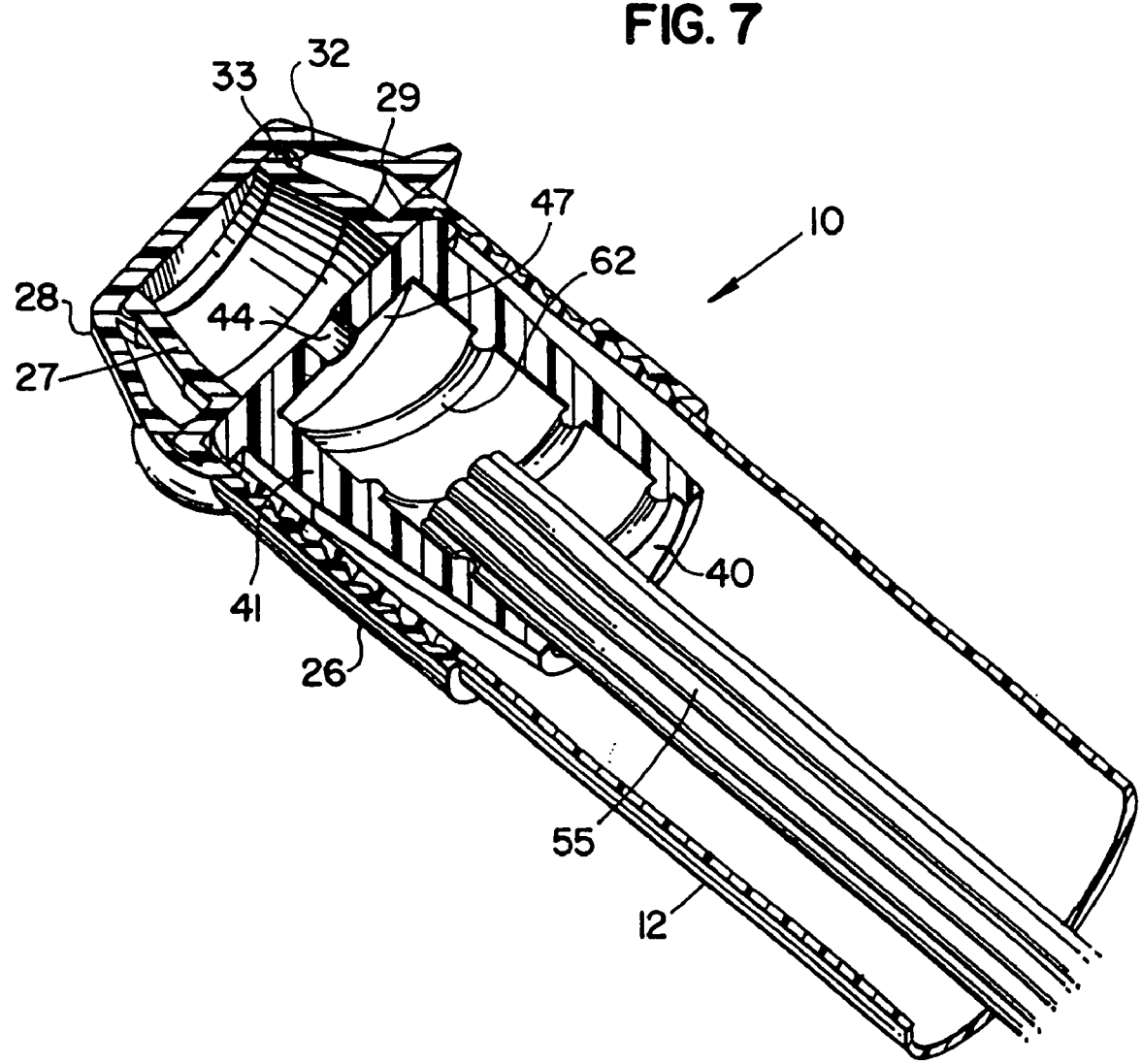
Figure 8:
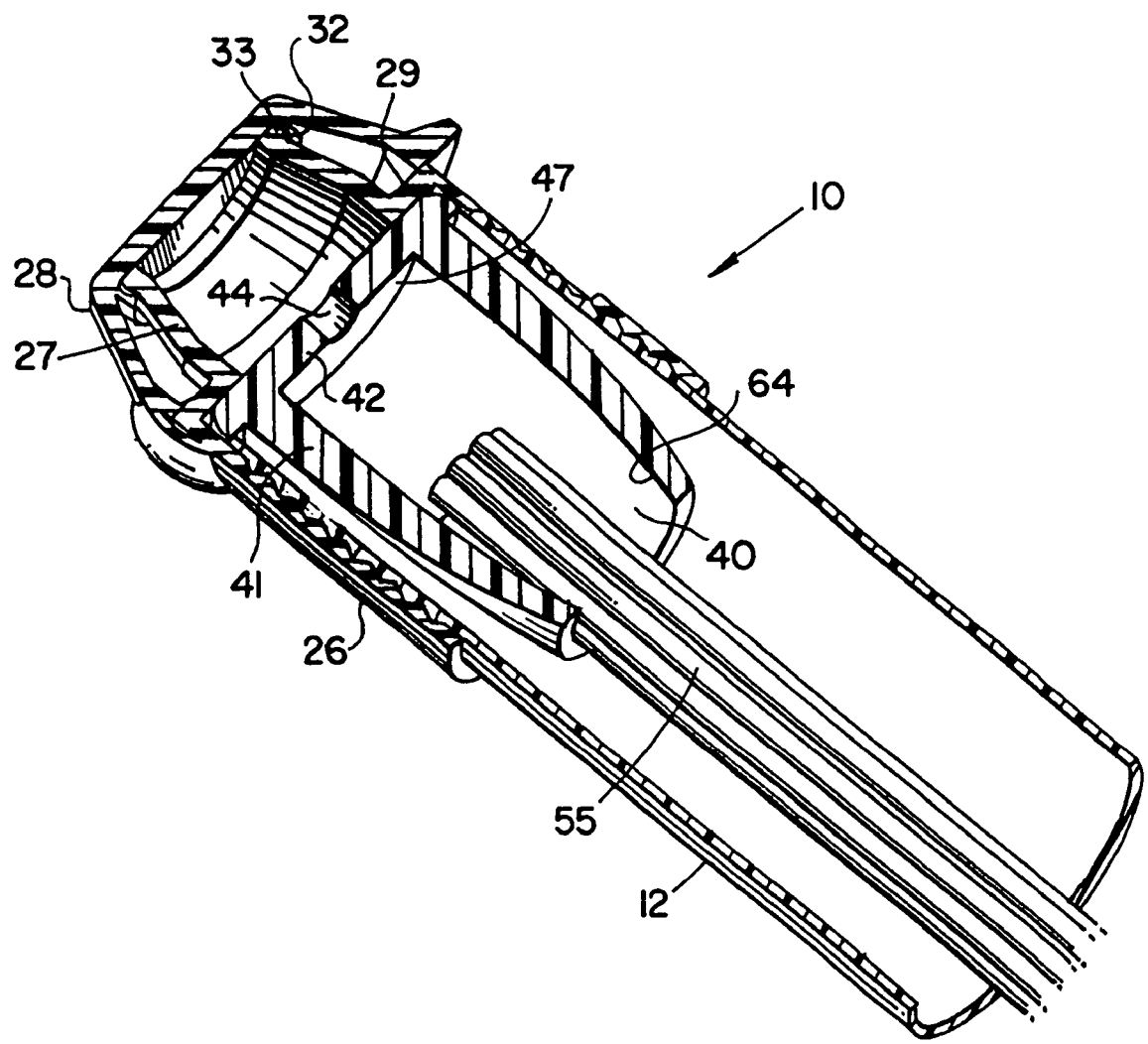
Figure 9:
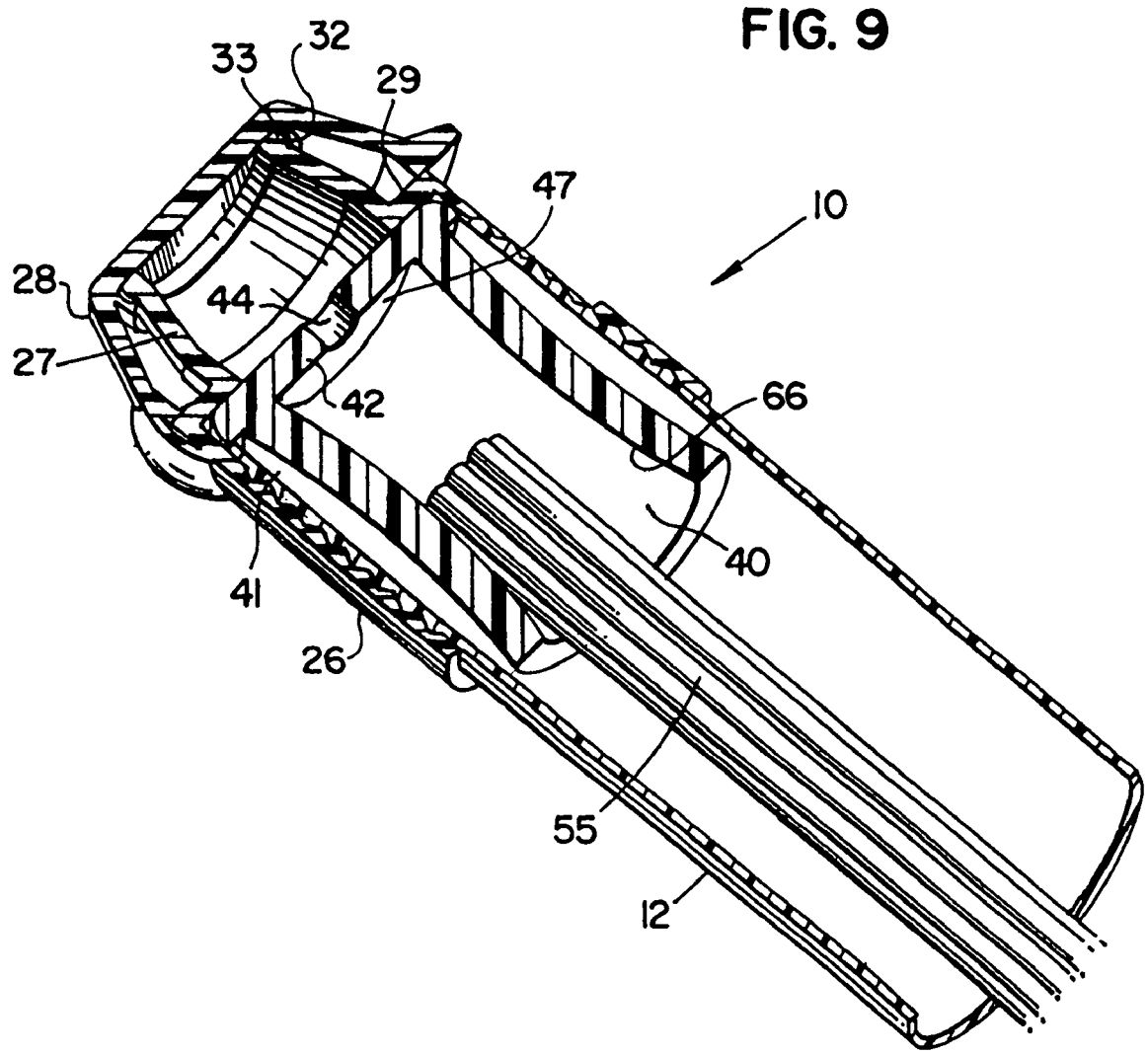
Figure 10:
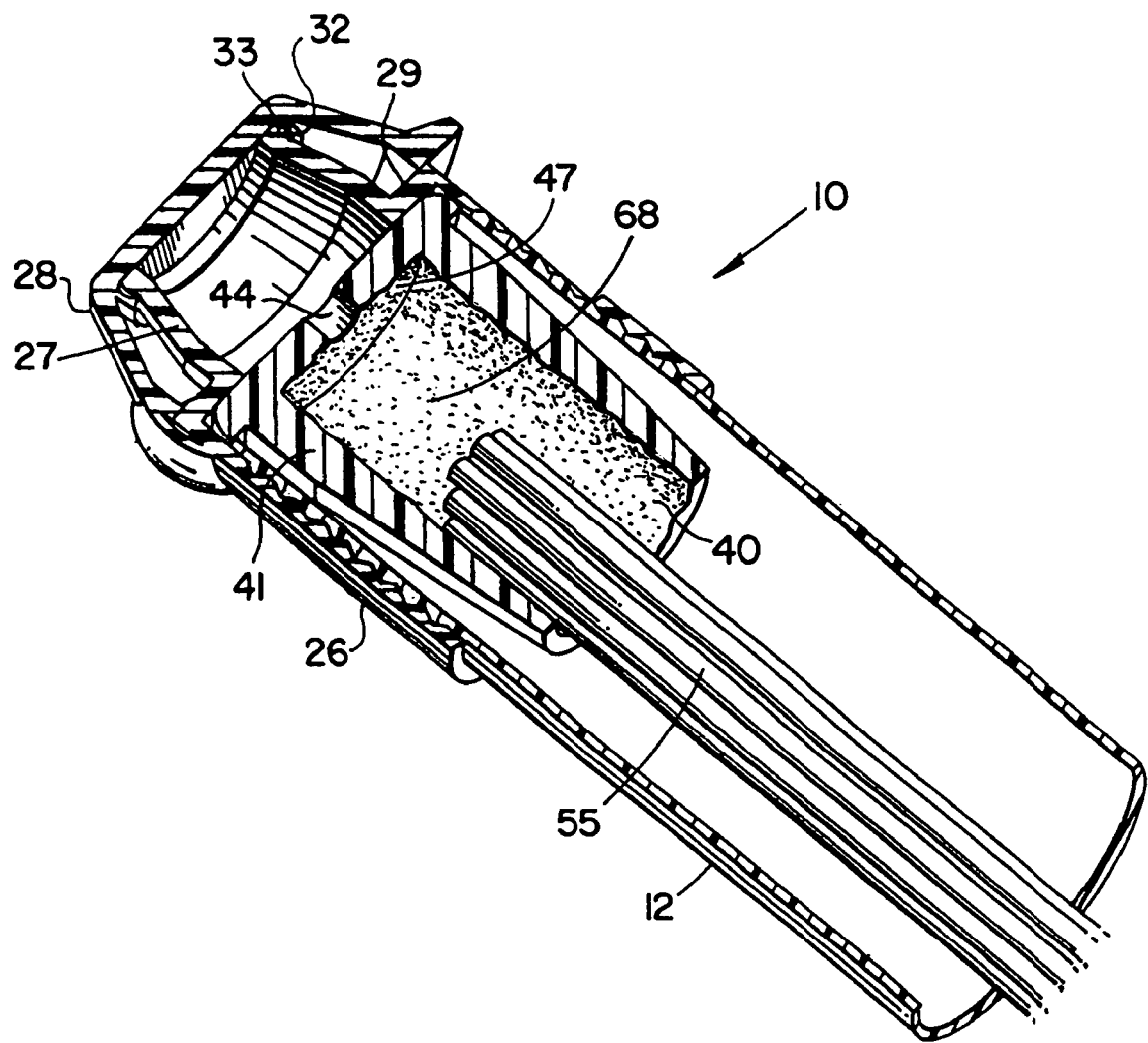
Figure 11:
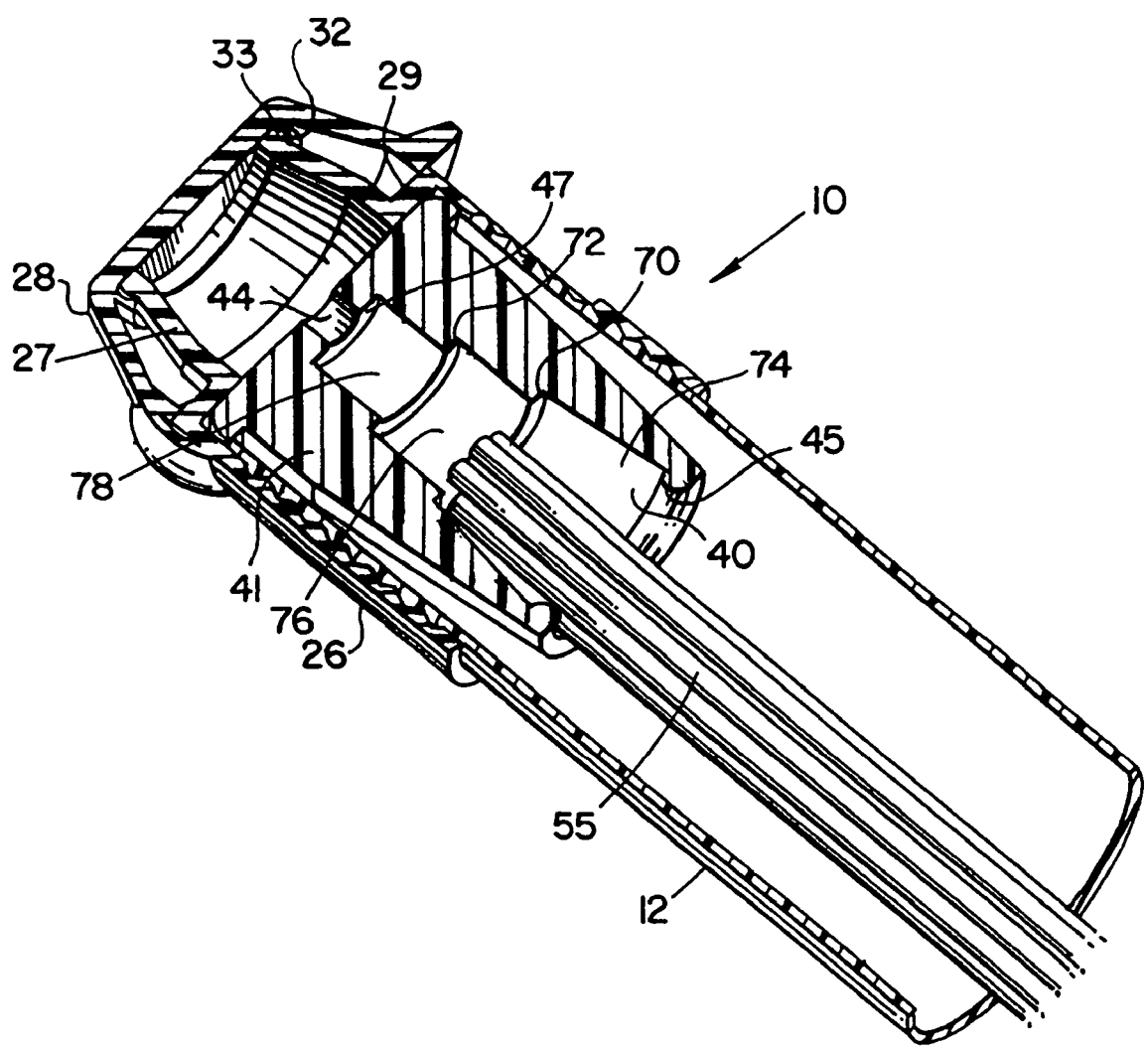

FIGS. 6-11 illustrate alternative designs of the inner wall surface 46 of reducing insert sleeve portion 41. With the exception of the inner wall surface designs noted herein, the remaining portions of holder may be the same as illustrated in FIGS. 1-5. In FIG. 6, a plurality of protrusions, such as pimples or bumps 60, are randomly distributed along inner wall surface 41. In FIG. 7, a generally spiral or helically shaped bead 62 extends along the inner wall surface. In FIG. 8, a portion of inner wall surface 41, such as lower wall portion 64, is inwardly directed to form a concave wall. In FIG. 9, a portion of inner wall surface 41, such as lower portion 66, is outwardly directed to form a convex wall. In FIG. 10, inner wall surface 41 is provided with an irregular surface, such as by forming a roughened texture 68 on the surface. In FIG. 11, inner surface is provided with one or more (in this case two) internal steps 70, 72, to provide a plurality (in this case three) surfaces 74, 76, 78 of decreasing diameter in the direction of aperture 44.

Those skilled in the art will appreciate that the inner wall surface features described herein need not be exclusive as shown in the figures, but rather, may be combined in any fashion. In addition, variations from the specific designs may be substituted.

As described and illustrated hereinabove, main holder body 12, reducing insert 14, and cap 16, are initially separate structures that are joined to form holder 10. However, these structures need not be formed separately, and they may alternatively be formed as an integral structure. As a still further alternative, any two of holder body 12, reducing insert 14 and cap 16 may be integral, and joined to the remaining component.

Figure 12:
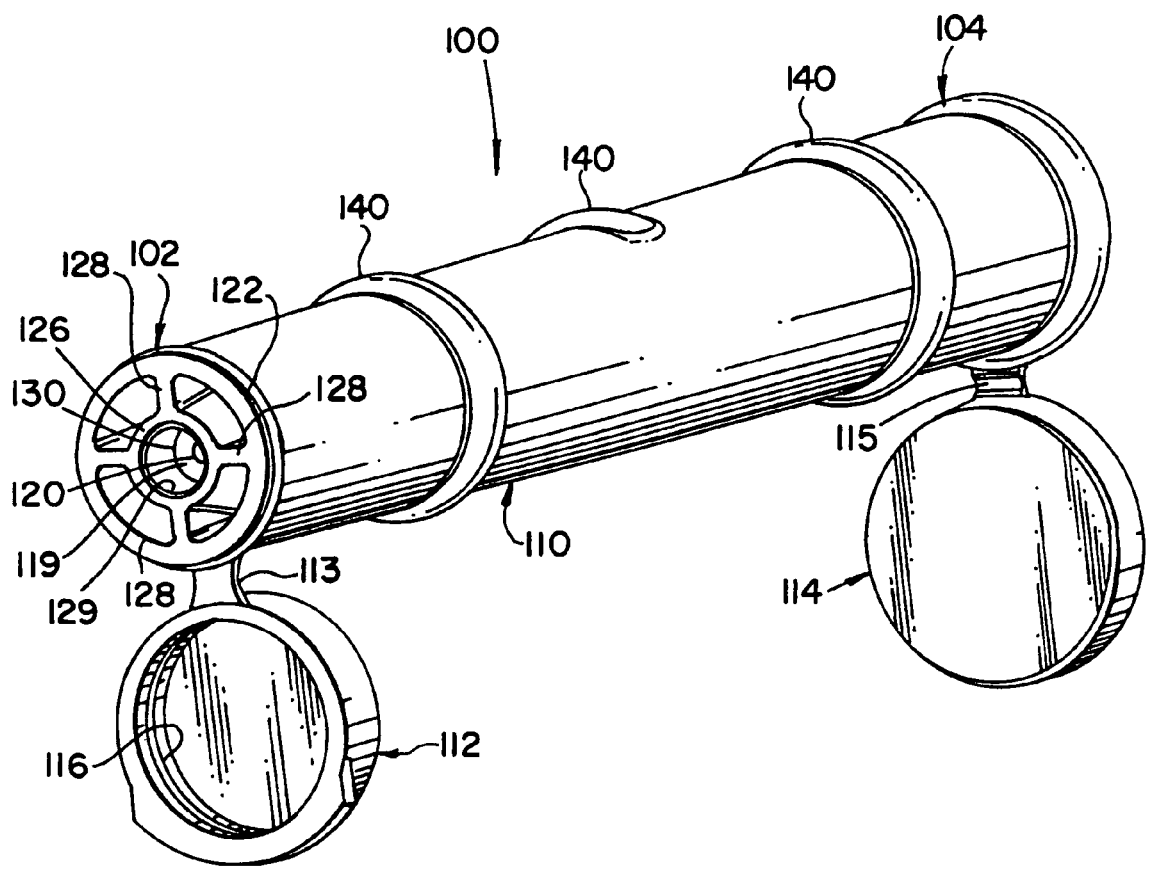
FIG. 12 is a perspective view of an integral pipette holder, according to another embodiment of the invention.

FIGS. 12-16 illustrate an embodiment of a holder 100 for a medical device, such as a pipette, that is formed as an integral structure. FIG. 12 illustrates a perspective view of holder 100. FIG. 13 illustrates a side view of holder 100, and FIG. 14 illustrates a sectional view of holder 100, taken along lines 14-14 of FIG. 13. FIG. 13 also illustrates some internal features of holder 100 in phantom. FIG. 15 illustrates an end view taken from end 102 of holder 100, and FIG. 16 illustrates an end view taken from holder end 104.

As shown in the figures, holder 100 comprises a main holder body 110, and respective end caps 112, 114. Each cap 112, 114 is attached to respective holder end 102, 104 by a suitable engagement mechanism that is structured to permit selective closure of respective ends 102, 104. In a preferred embodiment, the engagement mechanisms comprise living hinges 113, 115. Alternatively, other connection and closure mechanisms may be substituted. Similarly, it is not necessary in all embodiments that two end caps be provided. Rather, the main holder body can be sealed at one end, with a single end cap provided at the other end. As yet another embodiment, a single end cap can be formed to be integral with the main body, and another end cap can be removable, such as by a screw connection. However, an integral structure with two end caps is preferred.

As shown in FIGS. 13 and 14, main holder body 110 has a generally cylindrical internal circumference, and includes a portion 118 that tapers from a larger diameter to a smaller diameter in the direction of holder end 102. In the embodiment shown, tapered portion 118 terminates in a frusto-conical end 119 having an aperture 120 therethrough. In a preferred embodiment, aperture 120 is dimensioned to permit passage therethrough of only a single pipette at any one time.

Additional structure may be provided at holder end 102 to strengthen main holder body 110, and/or to guide a pipette for safe and easy removal from holder 100. In the embodiment shown, holder end 102 includes a ribbed frame that is formed from a plurality of spaced rib members 128. A terminal radial end of each rib member 128 meets to form an annular ring 129. Aperture 130 is disposed within the circumference of annular ring 129. Aperture 130 is sized to permit easy withdrawal of the pipettes from holder 100, and more particularly, from smaller diameter aperture 120. In a preferred embodiment, rib members 128, annular ring 129, and aperture 120 are axially inwardly offset (e.g., countersunk) from the axially outer edge of end portion 102. Offsetting the end portion in this manner reduces the possibility of contamination from inadvertent contact by the clinician when a pipette is being withdrawn from the holder.

In the embodiment shown in FIGS. 12-16, caps 112 and 114 are provided with internal rib members 116, 117, respectively. Rib members 116, 117 are sized and shaped for forming a snap fit with respective rib members 122, 123 on an external surface of main holder body 110 in conventional fashion. As with the previous embodiment, those skilled in the art will appreciate that other conventional attachment mechanisms, such as a friction fit, a threaded engagement, and the like, can be substituted for the snap fit shown in the figures.

As with the previous embodiment, main housing body 110 also preferably has a length closely approximating the length of the medical device(s), such as pipette(s), to be housed therein. Although a certain amount of axial movement of the pipettes is normally permissible, it is preferred to avoid undue movement to the extent possible to minimize the possibility of damage to the pipettes.

Holder main body 110 is preferably a hollow cylindrical-type structure, having a rigid or semi-rigid construction. Preferably, holder main body 110 has a slight taper from holder end 104 to holder end 102. Optional ribs 140 may be provided around the external surface of holder main body. It is believed that ribs 140 improve the dimensional integrity, as well as the grippability, of the holder device. Those skilled in the art will appreciate that the number, spacing, and size of ribs 140 may be varied for a particular purpose, with the arrangement in the figures merely representing one possible arrangement.

Preferably, holder main body 110 and end caps 112, 114 are formed from a moldable polymer, such as polypropylene. Those skilled in the art will appreciate that when an integral structure is formed to include one or more living hinges, it is generally preferred to mold the structure. However, when other arrangements are substituted, the main body need not necessarily be molded, but instead, can typically be formed by any other conventional technique. As stated, although it is preferred to form the living hinges to maintain end caps 112, 114 with holder main body 110, other conventional attachment techniques may be substituted.

As explained, in this embodiment the holder 100 shown in FIGS. 12-16 is an integral structure. This is advantageous from the standpoint that an integral structure may enable a user to minimize contamination of the internal structure of the holder, since the various segments of the holder are always attached. Thus, for example, when end cap 114 is opened to permit loading of one or more pipettes into holder 100, the end cap nevertheless remains attached to holder body 110 via living hinge 115. There is no necessity to remove the end cap and place it on an external surface from which it may become exposed to contaminants. Furthermore, it is apparent that the likelihood of misplacing the end cap is eliminated in the integral arrangement. Similarly, when end cap 112 is opened to remove a pipette from the holder, the end cap is simply snapped open, but otherwise remains attached to main holder body 110 via living hinge 113.

The holders described herein are capable of housing the pipettes in a clean, sterile and undamaged state. The holders can be used to safely transport the pipettes, and to minimize the buildup of static electricity. The holders also provide a controlled mechanism for safely dispensing a single pipette at a time, and in the substantial absence of contamination.

It is therefore intended that the foregoing detailed description be regarded as illustrative rather than limiting, and that it be understood that it is the following claims, including all equivalents, that are intended to define the spirit and scope of this invention.

The invention claimed is:

1. A holder for a pipette, comprising:
   an elongated main body portion, said main body portion comprising a closed axial end and an open axial end, said main body portion having an interior space and having a length suitable for housing at least one pipette therein;
   a reducing insert, said reducing insert comprising a sleeve having an open end and a substantially closed end having a substantially flat inner surface, said sleeve sized and arranged such that said sleeve open end is received in said interior space of said main body portion through said open axial end, said substantially closed end of said sleeve having an aperture extending therethrough and communicating with said interior space, said aperture having a diameter sufficient for passage of only a single pipette therethrough at any one time, wherein said sleeve open end has a smaller diameter and said substantially closed end has a larger diameter such that said substantially closed end is not receivable in said main body portion open axial end; and
   a cap, said cap comprising a base portion and a seal portion, said base portion engageable with said open axial end of said main body portion, said seal portion being hingedly engaged with said base portion and movable relative to said base portion between an open position wherein said interior space of said main body portion communicates via said aperture with an environment exterior of said holder, and a closed position wherein said seal portion covers said aperture.

2. The holder of claim 1, wherein said reducing insert is positioned in said holder such that a length between said main body portion closed axial end and reducing insert open end is less than a length of said pipette, and a length between said main body portion closed axial end and said substantially closed end of said reducing insert exceeds the length of said pipette.

3. The holder of claim 1, wherein said reducing insert sleeve has an inner sleeve surface, said insert further comprising a structure for spacing said pipette from said inner sleeve surface.

4. The holder of claim 3, wherein said structure comprises at least one of a spacing ring, a plurality of generally inwardly directed protrusions, a generally helically shaped bead, a generally concave shaped wall portion, a generally convex shaped wall portion, and a textured inner sleeve surface.

5. The holder of claim 1, wherein said reducing insert sleeve has an internal surface comprising a plurality of stepped surfaces of decreasing diameter in the direction of said aperture.

6. A kit for use in a medical procedure, comprising: at least one pipette suitable for use in said medical procedure; and a holder for said at least one pipette, said holder comprising a main body portion, a reducing insert, and a cap; said main body portion comprising a normally-closed axial end and an open axial end, said main body portion having an interior space and sized for holding said at least one pipette in said interior space; said reducing insert comprising a sleeve having a smaller diameter open end and a larger diameter substantially closed end having a substantially flat inner surface, said sleeve sized and arranged such that said smaller diameter open end is received in said main body portion open axial end and said larger diameter substantially closed end is not receivable in said main body portion open axial end, said substantially closed end having an aperture extending therethrough and communicating with said interior space, said aperture having a diameter sufficient for passage of only a single pipette therethrough at any one time, said pipette having a length such that it exceeds a length between said main body portion closed axial end and said open end of said sleeve and such that it is less than a length between said main body portion closed axial end and said substantially closed end of said reducing insert; said cap comprising a base portion and a seal portion, said base portion engaged with said open axial end of said main body portion, said seal portion hingedly engaged with said base portion and movable between an open position wherein said interior space of said main body portion communicates via said aperture with an environment exterior of said holder for removal of said pipette from said holder, and a closed position wherein said seal portion covers said aperture.

* * * * *

UNITED STATES PATENT AND TRADEMARK OFFICE
CERTIFICATE OF CORRECTION

PATENT NO. : 7,624,868 B2  Page 1 of 1
APPLICATION NO. : 11/602593
DATED : December 1, 2009
INVENTOR(S) : Booker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 267 days.

Signed and Sealed this

Twenty-sixth Day of October, 2010

David J. Kappos
*Director of the United States Patent and Trademark Office*